(12) United States Patent
Kieturakis

(10) Patent No.: US 9,949,790 B2
(45) Date of Patent: Apr. 24, 2018

(54) SINGLE PORT LAPAROSCOPIC ACCESS WITH LATERALLY SPACED VIRTUAL INSERTION POINTS

(71) Applicant: Maciej J. Kieturakis, Los Altos Hills, CA (US)

(72) Inventor: Maciej J. Kieturakis, Los Altos Hills, CA (US)

( * ) Notice: Subject to any disclaimer, the term of this patent is extended or adjusted under 35 U.S.C. 154(b) by 329 days.

(21) Appl. No.: 14/710,281

(22) Filed: May 12, 2015

(65) Prior Publication Data
US 2015/0238250 A1 Aug. 27, 2015

Related U.S. Application Data

(63) Continuation of application No. 13/167,194, filed on Jun. 23, 2011, now abandoned.
(Continued)

(51) Int. Cl.
*A61B 1/32* (2006.01)
*A61B 18/14* (2006.01)
(Continued)

(52) U.S. Cl.
CPC .......... *A61B 18/1482* (2013.01); *A61B 17/29* (2013.01); *A61B 17/3423* (2013.01); *A61B 2017/00738* (2013.01); *A61B 2017/00991* (2013.01); *A61B 2017/2902* (2013.01); *A61B 2017/293* (2013.01); *A61B 2017/2904* (2013.01); *A61B 2017/2905* (2013.01); *A61B 2017/3429* (2013.01); *A61B 2017/3445* (2013.01); *A61B 2017/3447* (2013.01);
(Continued)

(58) Field of Classification Search
CPC ........ A61B 17/3423; A61B 2017/3429; A61B 2017/3445; A61B 2017/3447
USPC .................................................. 606/205–208
See application file for complete search history.

(56) References Cited

U.S. PATENT DOCUMENTS

| | | | |
|---|---|---|---|
| 4,867,404 A | 9/1989 | Harrington | |
| 5,222,973 A | 6/1993 | Sharpe et al. | |

(Continued)

FOREIGN PATENT DOCUMENTS

| | | |
|---|---|---|
| CN | 101322640 | 12/2008 |
| JP | H09510382 | 10/1997 |

(Continued)

OTHER PUBLICATIONS

International search report and written opinion dated Feb. 2, 2012 for PCT/US2011/041691.
(Continued)

*Primary Examiner* — Diane Yabut
*Assistant Examiner* — Martin T Ton
(74) *Attorney, Agent, or Firm* — Wilson Sonsini Goodrich & Rosati

(57) ABSTRACT

A system for performing single port laparoscopic procedures includes a transcutaneous seal and a plurality of tools. The tools comprise a substantially rigid tubular seal having a core which is translatably and rotatably disposed in the sleeve. The handle at the proximal end of the tool controls an end effector at the distal end of the tool. The sleeves of the tools are locked in the transcutaneous seals so that they remain in a fixed geometric relationship which prevents the tools from interfering with each other during laparoscopic procedures.

9 Claims, 13 Drawing Sheets

Related U.S. Application Data

(60) Provisional application No. 61/358,548, filed on Jun. 25, 2010.

(51) Int. Cl.
  *A61B 17/29* (2006.01)
  *A61B 17/34* (2006.01)
  *A61B 17/00* (2006.01)
  *A61B 18/00* (2006.01)

(52) U.S. Cl.
  CPC ............... *A61B 2018/00172* (2013.01); *A61B 2018/00184* (2013.01)

(56) References Cited

U.S. PATENT DOCUMENTS

| | | | |
|---|---|---|---|
| 5,380,338 A | 1/1995 | Christian | |
| 5,386,818 A | 2/1995 | Schneebaum et al. | |
| 5,395,367 A | 3/1995 | Wilk | |
| 5,441,042 A | 8/1995 | Putham | |
| 5,454,787 A | 10/1995 | Lundquist | |
| 5,624,379 A | 4/1997 | Ganz et al. | |
| 6,454,783 B1 * | 9/2002 | Piskun | A61B 17/06066 606/1 |
| 6,669,696 B2 | 12/2003 | Bacher et al. | |
| 6,953,461 B2 * | 10/2005 | McClurken | A61B 18/14 606/206 |
| 7,090,683 B2 | 8/2006 | Brock et al. | |
| 7,147,650 B2 | 12/2006 | Lee | |
| 7,297,142 B2 | 11/2007 | Brock | |
| 2003/0208206 A1 * | 11/2003 | Gitis | A61B 17/3403 606/108 |
| 2003/0236549 A1 * | 12/2003 | Bonadio | A61B 17/29 606/205 |
| 2004/0138525 A1 | 7/2004 | Saadat et al. | |
| 2005/0277946 A1 | 12/2005 | Greenhaigh | |
| 2006/0089532 A1 | 4/2006 | Tartaglia et al. | |
| 2006/0111209 A1 | 5/2006 | Hinman et al. | |
| 2007/0049966 A1 * | 3/2007 | Bonadio | A61B 17/00234 606/206 |
| 2007/0208312 A1 | 9/2007 | Norton et al. | |
| 2007/0299387 A1 | 12/2007 | Williams et al. | |
| 2009/0326462 A1 | 12/2009 | Wingardner, III et al. | |
| 2010/0130826 A1 | 5/2010 | Piskun | |
| 2010/0234687 A1 | 9/2010 | Azarbarzin et al. | |
| 2012/0116362 A1 | 5/2012 | Kieturakis | |

FOREIGN PATENT DOCUMENTS

| | | |
|---|---|---|
| JP | 2000501632 | 2/2000 |
| JP | 2008520362 | 6/2008 |

OTHER PUBLICATIONS

Office action dated Feb. 12, 2015 for U.S. Appl. No. 13/167,194.
Office action dated Apr. 4, 2014 for U.S. Appl. No. 13/167,194.
Office action dated Jul. 30, 2013 for U.S. Appl. No. 13/167,194.

* cited by examiner

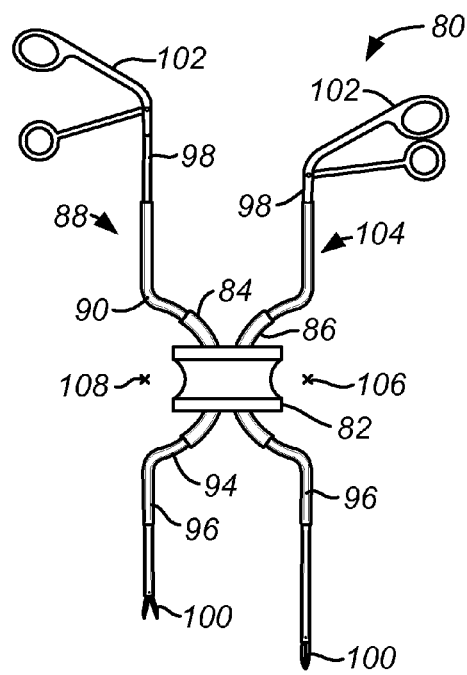
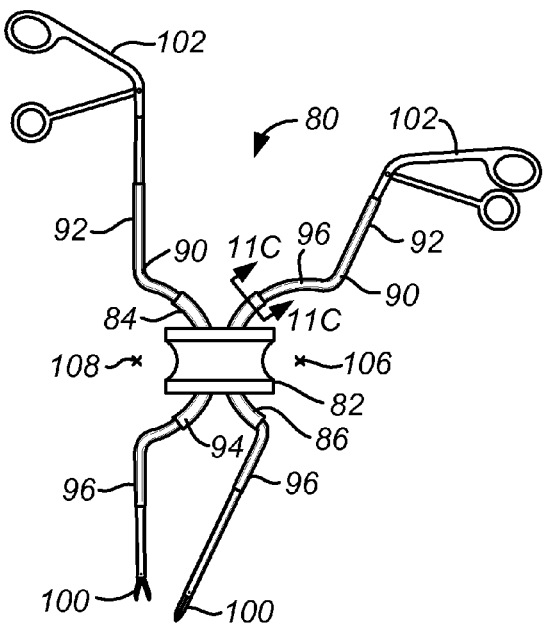
FIG. 11A    FIG. 11B
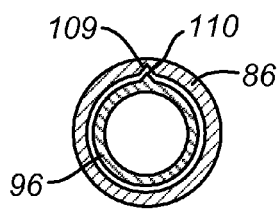
FIG. 11C

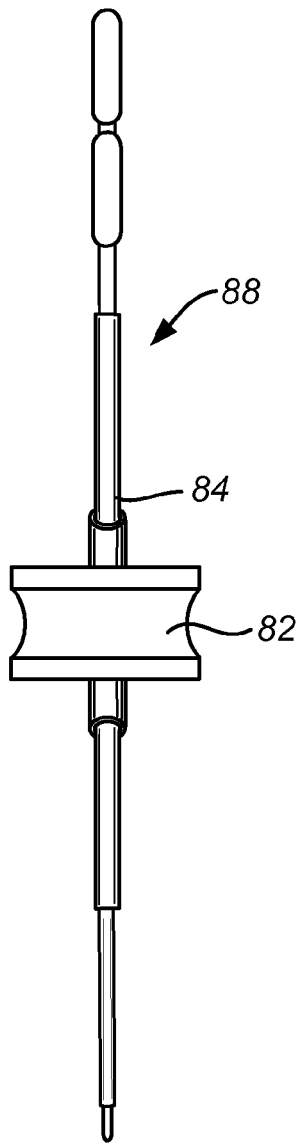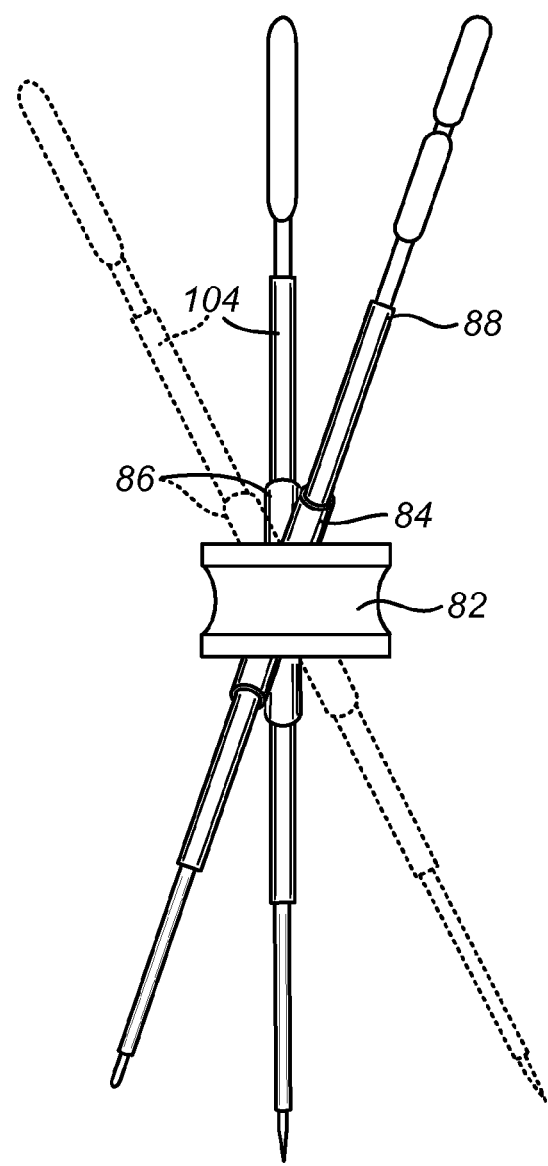
FIG. 12A  FIG. 12B

SINGLE PORT LAPAROSCOPIC ACCESS WITH LATERALLY SPACED VIRTUAL INSERTION POINTS

CROSS-REFERENCE TO RELATED APPLICATIONS

This application is a continuation of U.S. patent application Ser. No. 13/167,194, filed Jun. 23, 2011, now abandoned, which claims the benefit of provisional application No. 61/358,548, filed on Jun. 25, 2010, the full disclosure of which is incorporated herein by reference.

BACKGROUND OF THE INVENTION

1. Field of the Invention

The present invention relates generally to medical systems, tools, and methods. More particularly, the present invention relates to systems and tools for single port laparoscopic access, typically for access through the umbilicus or incisions.

In recent years, many open surgical procedures performed in the abdominal cavity have been replaced by minimally invasive procedures performed through several very small incisions using an endoscope, referred to as a laparoscope, inserted through one of the incisions. The other incisions are used for introducing surgical tools, and the abdominal cavity is inflated to create a space for performing the surgery. Such procedures are commonly called "laparoscopic", and can be used for gallbladder removal, hernia repair, hysterectomy, appendectomy, gastric fundoplication, and other procedures. Similar endoscopic, thoracoscopic and other procedures are performed in other body cavities without inflation.

While a great advance over open surgical procedures, which can require an incision of several inches or more through the abdominal wall, such laparoscopic procedures still require incisions through muscle or fascia in several separate sites. Each incision may increase the risk of infection, bleeding trocar site hernia, increased postoperative pain, compromised cosmetic result and other adverse events for the patient.

As an improvement over such laparoscopic procedures, "single port" laparoscopy has been proposed where a single access port is inserted through the umbilicus (the patient's navel). Access solely through the umbilicus is advantageous since it provides a superior cosmetic result. Introducing the laparoscope and all other tools necessary for the surgery through a single port, however, makes performance of the procedures more difficult. In particular, the use of conventional laparoscopic tools, which are typically straight, makes it difficult to approach a single target area in the treated tissue with two or more tools at the same time.

Thus, it would be a benefit to provide improved systems and tools for laparoscopic access through single ports for performing minimally invasive surgical procedures. It would be particularly desirable if the tools and other system components were able to facilitate access to target sites and reduce the likelihood that the tools would interfere with each other during the performance of the procedures. In particular, such tools and systems should further allow the physician to intuitively manipulate the tools, while viewing the procedure on the video display, in a manner similar to performance using more conventional multi-port laparoscopy procedures. At least some of these objectives will be met by the inventions described hereinafter.

2. Description of the Background Art

U.S. Patent Publ. 2007/0299387 describes a system for performing minimally invasive surgery through a single port where multiple cannulas are integrated in a single frame. U.S. Pat. No. 5,395,367 describes a single laparoscopic cannula having several tools passing therethrough. U.S. Pat. No. 6,454,783 describes a single port access system with curved cannulas that receive curved or S-shaped tools. Other patents and publications of interest include U.S. Pat. Nos. 7,297,142; 7,147,650; 7,090,683; 5,624,379; 5,441,042; 5,386,818; 5,380,338; and 4,867,404. A commercially available single port laparoscopic access system manufactured by TransEaterix, Inc., Durham, N.C. 27713, sold under the tradename Spider™, is described in "Instructions for Use—SPIDER Surgical Platform," copyright 2009.

BRIEF SUMMARY OF THE INVENTION

The present invention provides tools and systems for performing laparoscopic and other minimally invasive surgical procedures through a single port, typically a single port placed through the umbilicus. The tools and systems will be particularly useful for performing laparoscopic cholecystectomy, but also be suitable for performing other procedures such hernia repair, hysterectomy, colectomy, appendectomy, gastric fundoplication, and the like, as well as in thoracoscopic and extra-peritoneal procedures. The tools and systems are designed and optimized to minimize the likelihood that the individual tools will interfere with each other during performance of such minimally invasive procedures. In particular, the individual tools will be coupled to have limited movement relative to each other (but not necessarily with respect to the access port), and distal effectors will be manipulable relative to fixed portions of the tools. The coupling will prevent any rotation of inserted instruments in relation to each other at the same time allowing them to be freely movable in all directions within the plane vertical to the instrument. Typically, the distal effectors will be rotatable and translatable (advanceable and retractable) relative to a fixed portion of the tool. The coupled portion of the tool typically comprises a sleeve which defines the geometry which allows the tools to effectively approach a surgical site while minimizing the likelihood that the multiple tools present will interfere with each other during performance of the surgery. Additionally, the sleeves may be curved so that a middle region of each sleeve is transversely offset from distal and/or proximal regions of the sleeve so that the middle regions of adjacent tools converge to pass through a single laparoscopic seal while the proximal and/or distal regions remain spaced-apart to create laterally spaced apart virtual insertion points, i.e. the tools can be manipulated as if they passed through laterally spaced-apart access ports. Such tools may comprise various mechanisms for actuating the effector, for example opening and closing jaw-like tools, such as scissors, graspers, clamps, forceps, electrodes, and the like. In other instances, the tools may be static and not require manipulation other than advancement, retraction, and rotation, e.g., being retractors, hooks, needles, electrodes, and the like.

In a first aspect of the present invention, a laparoscopic tool comprises a tubular sleeve, a core disposed within a central passage of the sleeve, an effector at the distal end of the core, and a handle at the proximal end of the core. The tubular sleeve is substantially rigid and will define a geometry of the tool which provides both access to a surgical target site and clearance from other tools being used simultaneously to access the same site. The sleeve will have a proximal region defining an axis, a middle region extending from the proximal region, and a distal region extending from the middle region. The middle region has a proximal end attached to and extending from the proximal region, a distal end, and at least one curve between the proximal end and the distal end. In a first exemplary embodiment, the middle region will first curve away from the axis (defined by the proximal region) and then curve back toward the axis. The distal region will extend in a direction defined by the middle region toward the axis. Such S-shaped geometries will allow the proximal region of the tool which carry the handle to diverge away from a center axis defined by an access port while the distal regions of the tools which carry the effectors or operative tools will extend toward the center line which will typically be aligned with the desired surgical site. In a second exemplary embodiment, the middle region will have a C-shaped geometry with either substantially coaxial or substantially parallel proximal and distal regions. Tools with a C-shaped middle region and coaxially aligned, laterally offset proximal and distal regions are particularly useful for systems which provide laterally spaced virtual insertion points. Tools having U-shaped geometries will also find use.

The core will be designed to both transmit torque (where rotation of the handle about the tool axis will cause a like rotation in the distal end relative to the axis while the sleeve remains stationary) while being sufficiently flexible to navigate the non-linear middle region of the tubular sleeve. A variety of core constructions are suitable, typically having generally rigid proximal and distal sections joined by a middle section which is flexible but sufficiently torsionally stiff to be able to transmit torque. The flexible middle section can have a variety of specific constructions, such as a circumferentially reinforced polymeric tube, counterwound helical coils, or other known torquable tubes. In the illustrated embodiments, the middle section will comprise a plurality of nested elements which allow bending (in at least one direction but optionally in more than one direction) while transmitting torque regardless of the degree of bending.

When the effector is mechanically active, for example comprising an openable and closable jaw structure, the effector will be coupled to the handle to allow actuation. For example, a handle may comprise a trigger or lever mechanism joined to the effector by a cable and pull wire assembly, such as a Bowden cable, which is able to transmit an actuating force to the effector while conforming to the non-linear geometry of the laparoscopic tool and exerting little or no force on the core through which it is located. In other instances, where the effector is passive (not mechanically active), the effector may be coupled to the handle by the core itself. In cases where the effector is electrically active, an electrical cable can be provided between the handle and the effector to provide the necessary power.

In the illustrated embodiments, at least a portion of the proximal region of the sleeve will be substantially straight, typically the entire region being straight. Usually, at least a portion of the distal region will also be straight, with the exemplary embodiments including proximal and distal regions both of which are substantially straight. Often, the proximal and distal regions will lie on generally parallel lines (in some cases being co-linear, lying on the same line), but such parallel construction is not a requirement. Optionally, the proximal and distal regions can telescope to vary the "reach" or extension length of the tool.

Further, in one of the illustrated embodiments, the middle region of the sleeve has an S-shaped geometry with a proximal curve in one direction followed by a distal curve in the opposite direction. In other illustrated embodiments, the middle region has a C-shaped geometry, typically being curved at a constant radius and subtending an arc of about 180°. The sleeve will usually have a length in the range from about 18 cm to 35 cm, usually from 18 cm to 25 cm with the proximal region having a length in the range from 4 cm to 12 cm, usually from 5 cm to 10 cm, the middle region having a length in the range from 10 cm to 20 cm, usually from 12 cm to 16 cm and the distal region having a length in the range from 4 cm to 12 cm, usually from 5 cm to 10 cm. The proximal curve will usually have a radius in the range from about 3 cm to 12 cm, typically from 5 cm to 7 cm, with the distal curve having a radius in the range from 3 cm to 12 cm, typically from 5 cm to 7 cm. The outer diameter of the tools will typically be as small as possible while maintaining the necessary mechanical strength and ability to couple the distal effector to the handle. Usually, the tool diameter will be in the range from 2 mm to 10 mm, more usually from 4 mm to 6 mm.

In another aspect of the present invention, a laparoscopic system comprises a first tool, a second tool, and a transcutaneous seal having first and second coupled tubes which removably receive the first and second tools and optionally having additional tubes or ports for receiving a laparoscope and additional tools. The tools will usually each have a proximal handle segment, a middle segment, and a distal effector segment. The tubes will be adapted to maintain the middle segments of the tools in a coupled relationship, typically being in a fixed or pivoted relative orientation with respect to each other (and optionally with respect to additional tools) in order to present relative rotation and longitudinal displacement of the coupled tubes. In some embodiments the tools will be non-removably disposed in the tube and the tubes will have coupling elements that allow the tubes to be first attached and later detached and replaced with other tool/tube combinations.

A fixed or pivotally coupled orientation will typically orient the handles so that they diverge from each other in a proximal direction from the seal. The middle segments of the tools will converge through the seal and then diverge from each other in a distal direction away from the seal, and the distal effector segments will then converge back toward each other in the distal direction from the seal. By diverging the handles and the middle portions of the tools from each other, the likelihood of the tools interfering with each other during performance of the procedure is greatly diminished. By further longitudinally locking the tools in the receiving tubes, the chance of interference is further reduced.

A pivoted coupling of the tubes which maintain the tools in the laparoscopic seal will allow the "plane" of each tool to pivot relative to the plane of the other tool(s), typically pivoting about a horizontal axis to allow an additional degree of movement of the distal segments of the tools, as illustrated in more detail hereinbelow. The tools, however, will be prevented from rotating about their own axes relative to each other to maintain a stable platform for manual manipulation of the effectors.

In some embodiments, the sleeves of tools will be locked within the receiving tubes of the seal so that the sleeves are not free to slide and rotate relative the laparoscopic seal. The tool cores of course remain free to translate and rotate within the sleeves and, when the receiving tubes are pivotally mounted relative to the seal, the tools will further be able to move in all directions within a plane vertical to each of the tool in any given tool position. In such cases, the spatial displacement of the tool effector within the body cavity will be achieved by combination of manipulation of tool axis in any desired location (e.g. medial/lateral or superior/inferior and by axially translating and rotating the tool core within the tool sleeve even when the sleeve is locked in the laparoscopic seal tube.

In other embodiments, however, it is beneficial to allow the tool sleeve to slide within the laparoscopic seal tube while preventing rotation of the sleeve relative to the tube. This can be achieved by employing a relatively long C-shaped tube which receives a similarly shaped C-shaped sleeve of the tool. In other cases, a track, groove, or other alignment member may be provided to allow sliding of the tool within the tube while preventing rotation of the tool about its own axis relative to the tube.

In the systems of the present invention, the handles will be used to manipulate the distal effector segments, typically allowing both rotation and translation (both advancement and retraction). The handles will usually further provide triggers, levers, or other manually deployed actuators coupled to the distal effectors, typically jaw-like tools, such as scissors, forceps, electrodes, and the like.

The transcutaneous seal of the laparoscopic system will typically be adapted for placement in the umbilicus. An exemplary and preferred seal comprises a polymeric block with passages for removably receiving the first and second tools, as well as optionally further tools and a laparoscope or other endoscope.

The system may further comprise individual locks for securing each tool in a passage of the seal, where the locks are usually coupled to each other to hold the tools in a fixed orientation in a plane vertical to a pivotal axis of the tools when the tools are locked in the seal, preferably at all times during performance of a procedure. In other instances, however, it will be possible to provide other mechanisms for locking the tools relative to each other. For example, a bridge or other mechanical link could be provided between the proximal ends of the tools, which could be removably secured after the tools have been introduced into the seal. In most instances, the tools will be removable and replaceable within the transcutaneous seal, but in some instances it might be desirable to perform systems with the individual tools fixed within the seal. In other instances, as described above, the sleeve of the tool will be able to slide freely within a pivoted plane (usually defined by the shape of the tube which receives the sleeve of the tool) while rotation of the tool about its own axis is inhibited. The ability to slide the tool within the seal tube is particularly beneficial when the seal tube has an arcuate profile (preferably curved with a uniform radius) which is matched by a similar arcuate profile of the middle region of the sleeve of the tool which is received. This allows a further degree of freedom in movement of the end effector of the tool while still limiting the likelihood that the tools will interfere with one another and maintaining the natural or intuitive feel of using the tools for the treating physician.

In another embodiment, the pivoted C-shape receiving tubes may have a fixed curve and may be non-removably received over the curved portion of the rigid tool sleeve. Thus, the receiving tube becomes an integral part of the tool eliminating the need to insert and remove the tool from the receiving tube. As each tool has it's own receiving tube, however, it is necessary that the tubes have couplers for fixedly or pivotally attaching individual tubes to each other. If male and female couplers are used, the left handed tool will be equipped with the c-shape tubing having the female half of the pivot and the right hand tools will be equipped with the male part of the pivot or vice versa. The assembly of the pivot will take place during insertion of the tools into the seal. Such pivot will be quickly engaged or disengaged with the quick release anchor being the part of the female or male part of the pivot. Such embodiment will further assure the precise radius match of the tool and the pivot tubing translating into sliding of the tool within the pivot tubing with the least friction and resistance. To facilitate a prompt selection of appropriate tools all left hand tools will be visibly marked in one color (e.g. green) and the right hand tools in another color (e.g. red). In other cases, however, it will be possible to employ "universal" coupling elements that allow any tool to attach—to any other tool. In still other embodiments, all tools may employ a common type of coupling element and a central coupling hub may be provided to receive two, three, four, or more tools at a time. In all cases, the coupling elements will usually provide for pivotal attachment, but in some instances they could alternatively provide for fixed attachment to each other and/or a central hub.

When the transcutaneous seal is formed from a polymeric material, the material will usually be sufficiently pliable and compliant so that the tools may be moved together within the seal. Thus, even thought individual tools will be fixed relative to each other, their position within the abdominal or other body cavity can be adjusted by moving the tools within the seal or optionally moving the entire seal within the umbilicus or other access location through tissue.

In the system described above, it would be preferable to use the particular tools which have also been described above. It should be noted, however, that the tools of the present invention may be used in systems other than the systems of the present invention, and that the systems of the present invention may employ tools which are different than the specific tools described with respect to the present invention.

In a still further aspect of the present invention, a transcutaneous seal comprises an elastomeric seal and at least a first shapeable tube extending axially therethrough. The elastomeric seal body is adapted to be positioned in the transcutaneous penetration in order to establish laparoscopic, thoracoscopic, and similar minimally invasive access. The first shapeable tube will have a central passage for removably receiving laparoscopic and similar tools for performing minimally invasive surgery. The first shapeable tube is particularly adapted to receive laparoscopic and other tools having non-linear geometries which would be difficult to advance and retract from rigid tubes within the elastomeric seal body.

In specific embodiments of the transcutaneous seal of the present invention, at least a second shapeable tube (or non-shapeable in some cases) may be positioned axially through the elastomeric seal body and will have a central passage for removably receiving laparoscopic and other tools in a manner similar to the first shapeable tube. The first and second shapeable tubes will preferably be attached to each other at at least one location along their lengths, optionally being pivotally attached so that the tubes may move with at least two degrees of freedom relative to each other, but usually being fixedly attached so that the tubes may not move relative to each other (but will be free to move within the elastomeric body itself within the elastic limits of the body). Usually, the first and second shapeable tubes will include a lock for axially securing the laparoscopic tool(s) within the respective tube, where the locks may be similar to those described for other embodiments of the present invention. In still further specific embodiments, the shapeable tubes will comprise a lubricious polymer, usually an inelastic lubricious polymer, such as polyethylene polyterephthalate (PTFE) which further facilitates introduction and removal of the tools through the tubes. Optionally, the lubricious polymer tubes may include a series of peripheral openings along an axial line on one side to allow preferential bending of the tube in a single plane. In the illustrated embodiments, each of the two shapeable tubes will have such peripheral openings and will be attached at locations peripherally opposite to the axial lines of openings so that both tubes preferentially bend in the same plane.

BRIEF DESCRIPTION OF THE DRAWINGS

FIGS. 11A and 11B are side views of a system constructed in accordance with the principles of the present invention including a transcutaneous seal having first and second laparoscopic tools slidably inserted through curved tubes in the seal.

FIG. 11C is a cross-sectional view taken along line 11C-11C of FIG. 11B.

FIGS. 12A and 12B illustrate a system constructed in accordance with the principles of the present invention including a transcutaneous seal having first and second laparoscopic tools inserted in tubes, where the tubes are able to pivot relative to each other to further allow repositioning of the end effectors while minimizing the risk of tool interference.

DETAILED DESCRIPTION OF THE INVENTION

Figure 1:
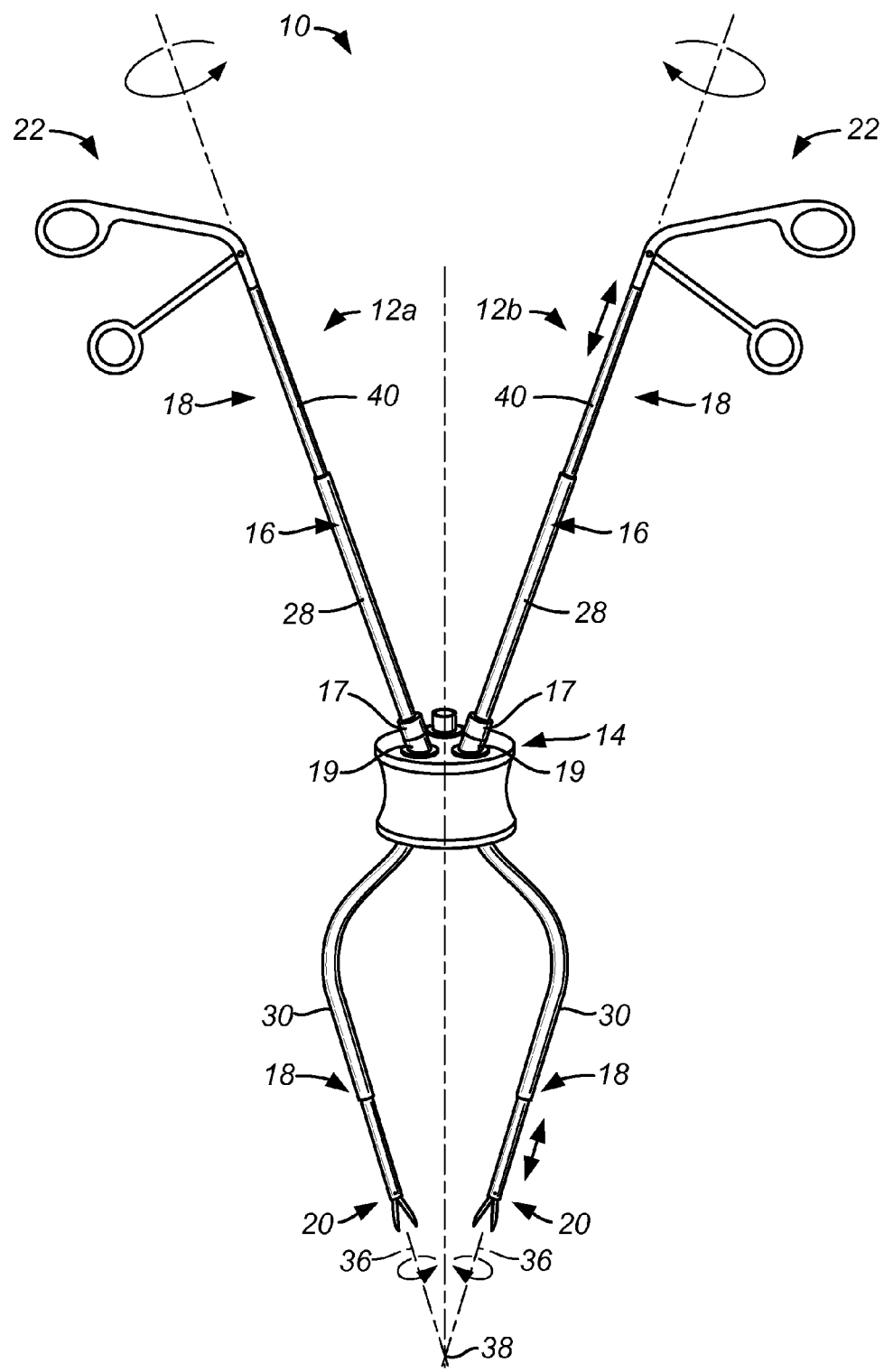
FIG. 1 is perspective view of a system constructed in accordance with the principles of the present invention including a transcutaneous seal having first and second laparoscopic tools inserted therethrough.
Figure 2:
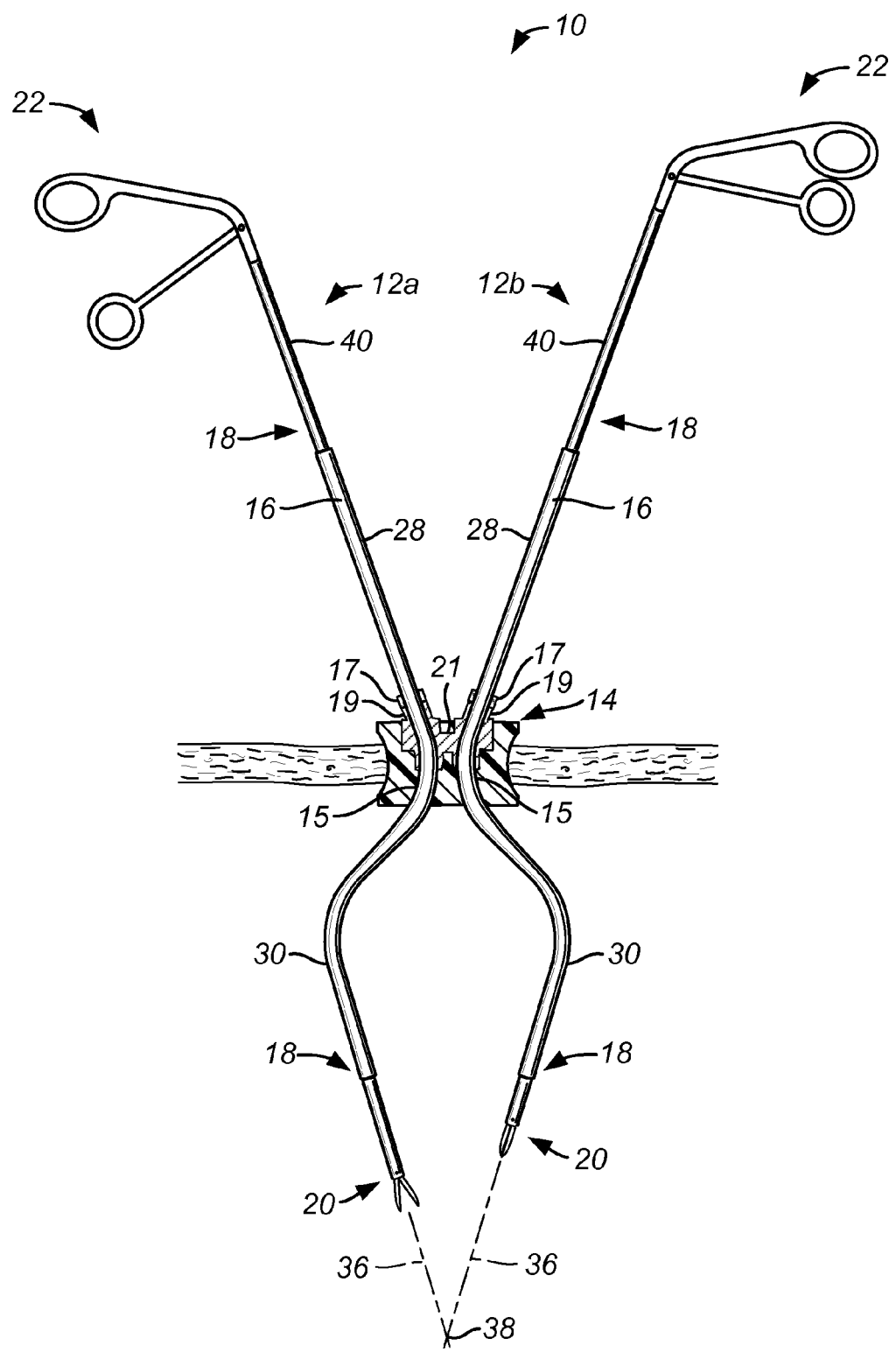
FIG. 2 is a cross-sectional view of the system of FIG. 1 shown with the port inserted through a patient's umbilicus.

Referring to FIGS. 1 and 2, a laparoscopic access system 10 constructed in accordance with the principles of the present invention comprises a first tool 12a, a second tool 12b, and a transcutaneous seal 14. Each tool 12a/b is shown with an identical construction, but it will be appreciated that the tools may differ in certain respects, particularly by having different end effectors and functions. In the illustrated embodiments, each tool, as further shown in FIGS. 3 and 4, comprises a tubular sleeve 16, and a core 18 having a distal effector 20 positioned at its distal end. A handle structure 22 is disposed at the proximal end of each core 18 and is mechanically coupled to the distal effector 20 by a connector cable 24, as shown in FIG. 4. The nature of the connector cable 24 will depend on the purpose and structure of the distal effector 20. When the distal effector 20 is mechanically actuable, the cable 24 will typically comprise an outer tube and inner wire (a Bowden cable) to allow closing of the handle 22 to retract the wire and drive the tool. Examples of such tools are scissors, graspers, clamps, forceps, electrodes, and other jaw-like effectors which may open and close by opening and closing the lever or trigger of the handle structure 22. If the distal effector 20 is electrically active, such as an electrode, resistance heater, motor driven element, or the like, cable 24 can be an electrical cable to provide the necessary electrical power.

The tubular sleeve 16 will be substantially rigid, typically formed from a metal, such as stainless steel, or a rigid polymer. The sleeve 16 typically includes a substantially straight proximal region 28 which extends distally from the transcutaneous seal 14, as seen in FIGS. 1 and 2. The sleeve 16 further includes a substantially straight distal region 30 which extends distally from a middle region 32 which includes a first curved segment having a radius $R_1$ and a second curved segment having a radius $R_2$. The preferred radii of these sections are set forth above. Such an S-shaped geometry provides for an optimum positioning of the handles 22 and of the effectors 20, as seen in both FIGS. 1 and 2. While an S-shaped geometry with axial or parallel end segments is illustrated, it is also possible to utilize a C-shaped geometry with diverging handles and distal tips, which design may be preferred by some physicians as mimicking more traditional laparoscopy. The handles 22 diverge over the transcutaneous seal 14 so that the physician can grasp them with the hands spaced will apart. In contrast, the effectors 18 converge along lines 36 to access a target location 38 at which procedures can be performed on patient tissue. In particular, the handles may be advanced and retracted in distal and proximal directions, respectively, to bring the tools to the common target site 38. When at the site, the tools may be rotated using the handles and/or the effectors may be actuated by opening or closing the lever trigger or mechanisms on the handle, as best seen in FIG. 2. In particular, tool 12a is shown with the jaw-elements of effector 20 open and the effector advanced partially toward the target site 38. In contrast, tool 12b is shown with the handle and effector 20 closed and the tool core withdrawn proximally from the target location 38.

The core 18 will have substantially rigid sections at each end and a substantially flexible central section which is positioned within a central passage of the sleeve 16. As shown in FIG. 4, a straight, rigid proximal section 40 is joined to a straight, rigid distal section 42 by a torque-transmitting, flexible central section 44. The core itself is hollow and has a central passage through its entire length. The central passage of the core receives the cable 24 (FIG. 4) with the handle 22 attached to the upper end 46 of the core 18. The effector 20, in turn, is attached to the lower end 48 of the core 18. The cable 24 is flexible and can accommodate changes in the curvature of flexible section 44 when the core 18 is disposed within the sleeve 16.

Figure 5:
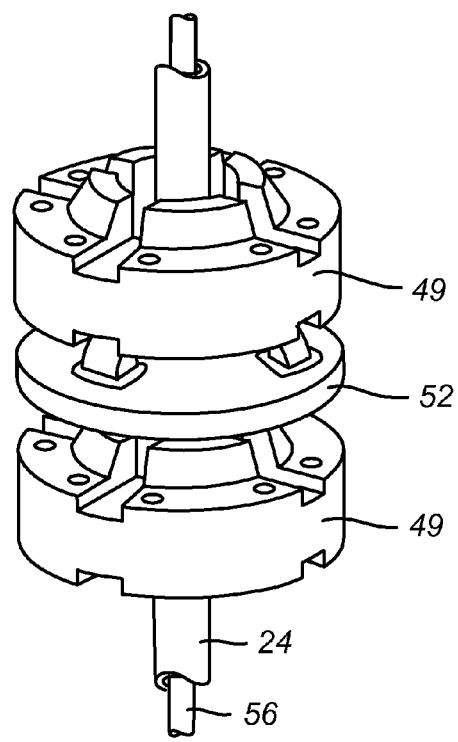
FIG. 5 illustrates a particular linkage construction which can be utilized in the flexible section of the core of the laparoscopic tool.

An exemplary embodiment of the flexible section 44 of the core is shown in FIG. 5 comprising a plurality of nested elements 49 and 52, which elements are able to bend or flex in any direction relative to each other while transmitting torque a proximal end of the column of elements is rotated about its axis by rotating handle 27. The cable 24 includes a pull tether 56 which passes through a central passage. The specific construction of such flexible, torque-transmitting elements is well known in medical arts and described in the patent and medical literature. An example of such torque-transmitting structure is described, for example, in U.S. Patent Pub. 2006/0111209, the full disclosure of which is incorporated herein by reference.

These tools and systems will be used in a variety of minimally invasive procedures, but are particularly useful in performing single port laparoscopic procedures. Such procedures may be performed by first making an incision in the umbilicus and locating the transcutaneous seal 14 therein, as illustrated in FIG. 2. As patient anatomy may vary, it is desirable to measure a distance between the transcutaneous seal 14 and the gallbladder neck, for example, by using measuring rods passed through a passage of the seal. Based on the distance, the length of the tools to be used can be selected. The tools may be available in several length ranges, for example from 10-12 cm, from 12-14 cm, from 14-16 cm, or the like. Different tools having different lengths may be used for different procedures and/or to accommodate anatomical variations among patients. Particular tools may then be introduced through the passages 15 in the transcutaneous seal 14. The tools will be locked in place, typically by engaging lock element 17 on each tool against a corresponding lock 19 which is part of the transcutaneous seal 14. As best seen in FIG. 2, the locks 19 are preferably rigidly held together, for example by a bridge 21 passing therebetween. In other embodiments (which are not illustrated), however, the sleeves 16 may be locked together by their clamps or mechanisms which can be deployed, usually on the proximal portions of the sleeves which are above the transcutaneous seal after the sleeves have been locked into place. In all instances, it will be necessary to lock the sleeves together in order to maintain a fixed geometry so that the effectors of the tools will not interfere with each other when they are being deployed and manipulated using the handles.

Figure 6:
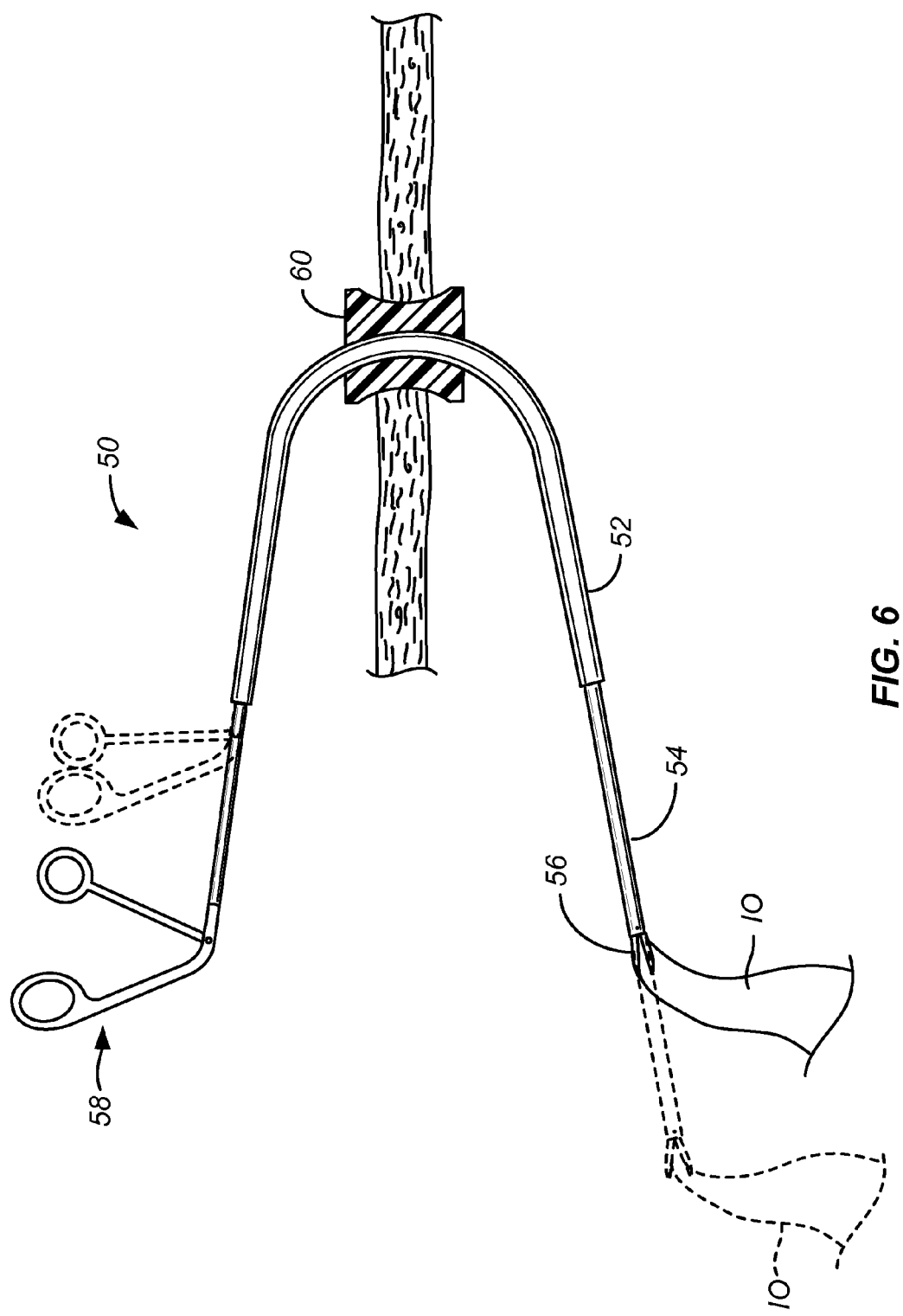
FIG. 6 illustrates an alternative construction of a laparoscopic tool constructed in accordance with the principles of the present invention, having a U-shaped middle region.

After the tools are in place, the removal of gallbladder can be performed using general known surgical techniques. Retraction of the organ (e.g. gallbladder) could be accomplished by percutaneous placement of an anchoring suture, insertion of standard mini grasper remotely to the umbilical single port incision or placement of the intraperitoneal clips. Alternatively, the gallbladder could be retracted using a particular U-shaped grasper, as illustrated in FIG. 6 hereinafter. Thus, during the procedure, it mayl be necessary to unlock the tools and replace them, either individually or in pairs. At all times, however, it will be necessary to maintain the rigid fixation of the right and left hand tool sleeves relative to each other so that the tools may be used and deployed without interference.

A laparoscopic tool 51 representing an alternative embodiment of the present invention is illustrated in FIG. 6. Laparoscopic tool 50 includes a tubular sleeve 52 having a core 54 with a distal effector 56. The handle structure 58 is operably connected to the core 54 at a proximal end opposite to the distal effector 56. The tool 50 may be introduced through a percutaneous seal 60 to provide for laparoscopic access into the abdomen or other body cavity. For example, the transcutaneous seal may be constructed in accordance with the embodiment described in FIGS. 7-10 below.

The laparoscopic tool 50 differs from those described previously principally in the shape of the tubular sleeve 52. The tubular sleeve 52 is generally U-shaped, and this design is particularly useful for retracting intercavity organs during a single port laparoscopy procedure, although it may be used in multiple port procedures as well. The U-shape can be useful to even further remove the handle 58 from the region of other tools being manipulated by the user. The core 54 may generally have the identical construction of core 18 shown in FIG. 4, and will be able to move in and out of the U-shaped sleeve 52 by moving the handle 58, as shown between the full line and broken line portions of the figure. The U-shaped sleeve 52 will usually include a lock component (not illustrated) so that it may be locked and immobilized with the transcutaneous seal and typically with other tools being introduced simultaneously through the seal. Retraction of a intracavitary organ IO can be accomplished by advancing and withdrawing the handle 58 to allow the end effector 56 to engage and retract the organ.

Figure 7:
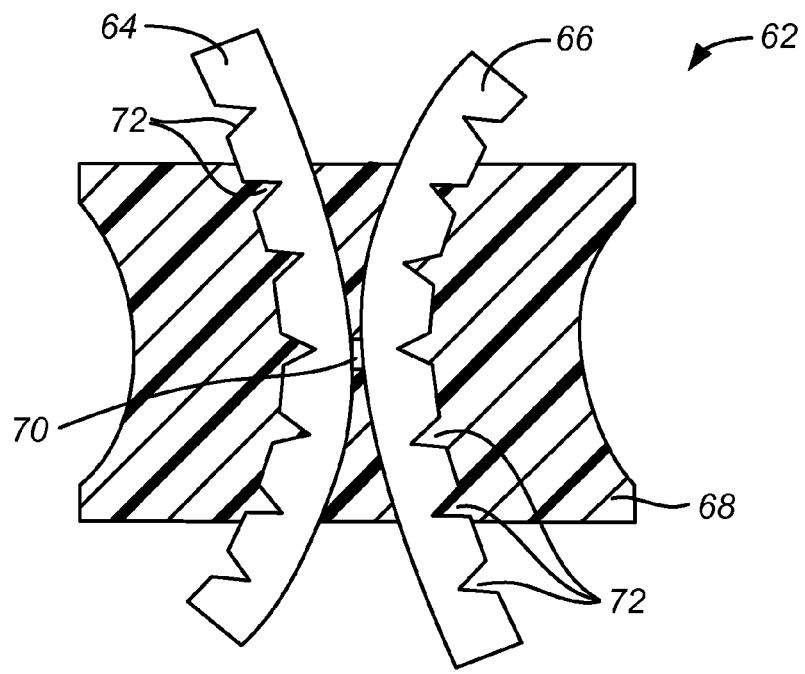
FIG. 7 illustrates a transcutaneous seal in accordance with the principles of the present invention having a pair of bendable tubes positioned therein.

Referring now to FIG. 7, a transcutaneous seal 62 constructed in accordance with the principles of the present invention comprises a first shapeable tube 64, a second shapeable tube 66, present in an elastomeric seal body 68. The first and second shapeable tubes 64 and 66 are connected by a connector 70, which may in some cases be fixed so that the tubes are held rigidly relative to each other, at least at the point of attachment. More usually, however, the connector 70 will allow pivotal movement of the first and second tubes 64 and 66 as shown generally in FIGS. 8 and 9. The tubes 64 and 66 will usually have an arcuate shape with the convex side of the curves located adjacent each other and the concave sides of the curves facing away from each other, generally as shown in FIG. 7. The tubes will be shapeable to permit introduction of the tool sleeves, as discussed in more detail below with respect to FIGS. 10A and 10B, and will have the curved profile so that a curved portion of the middle region of the sleeve of the tool can be received therein. As with prior embodiments, the sleeves may be locked relative to the tubes 64 and 66. In other, preferred embodiments, the sleeves will be able to slide within the curved tubes 64 and 66, as discussed below with reference to FIGS. 11A-11C. When the curved section of any tubular sleeve of a tool is present within the curved section of either tube 64 or 66, the tool will be able to slide along the curve but will be prevented from rotating.

Each of the first and second shapeable tubes 64 and 66 will be "shapeable," i.e. able to bend and conform with a laparoscopic or other interventional tool as the tool is advanced through the tube. Usually, in their unbiased or unstrained condition, i.e. without a tool in place within a central lumen thereof, each of the shapeable tubes 64 and 66 will have a generally curved configuration, as shown in FIG. 7, usually, this curved configuration will match that of the middle region of the sleeve of the tool to be introduced. The shapeable tubes 64 and 66, however, will be fabricated from materials and have geometries chosen so that they may straighten relatively easily. For example, each of the tubes may have a plurality of peripheral openings 72 allowing the long one axial length on the side of the tube, as shown in FIG. 7. These openings make it easier for the tube to straighten as a tool in introduced, as will be described in detail later. The shapeable tubes 64 and 66 will typically be composed at least in part from a lubricious polymer, such as polytetrofluoroethylene (PTFE) to further facilitate introduction and removal of laparoscopic and tools through the central passages or lumens of each tube.

Figure 3:
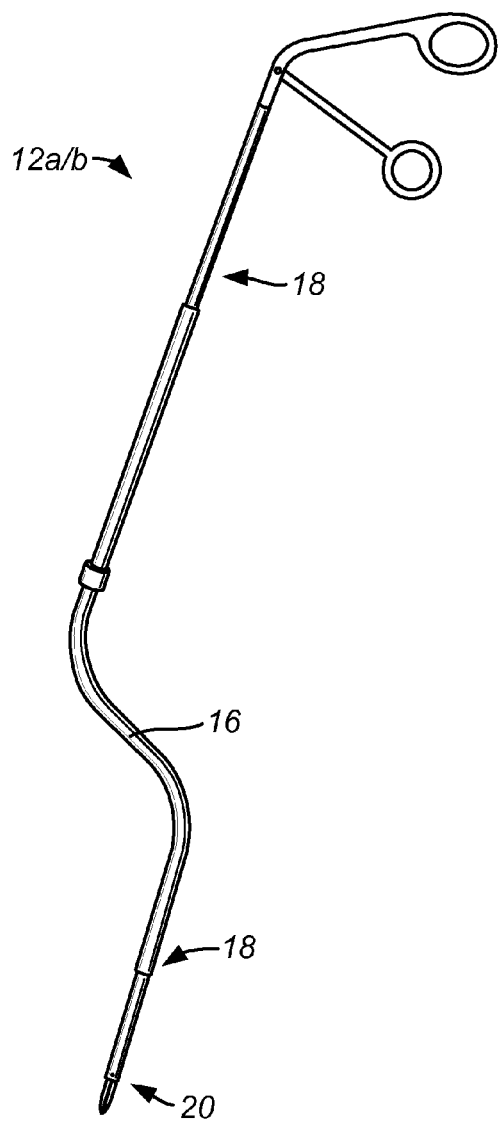
FIG. 3 illustrates a single tool constructed in accordance with the principles of the present invention.
Figure 4:
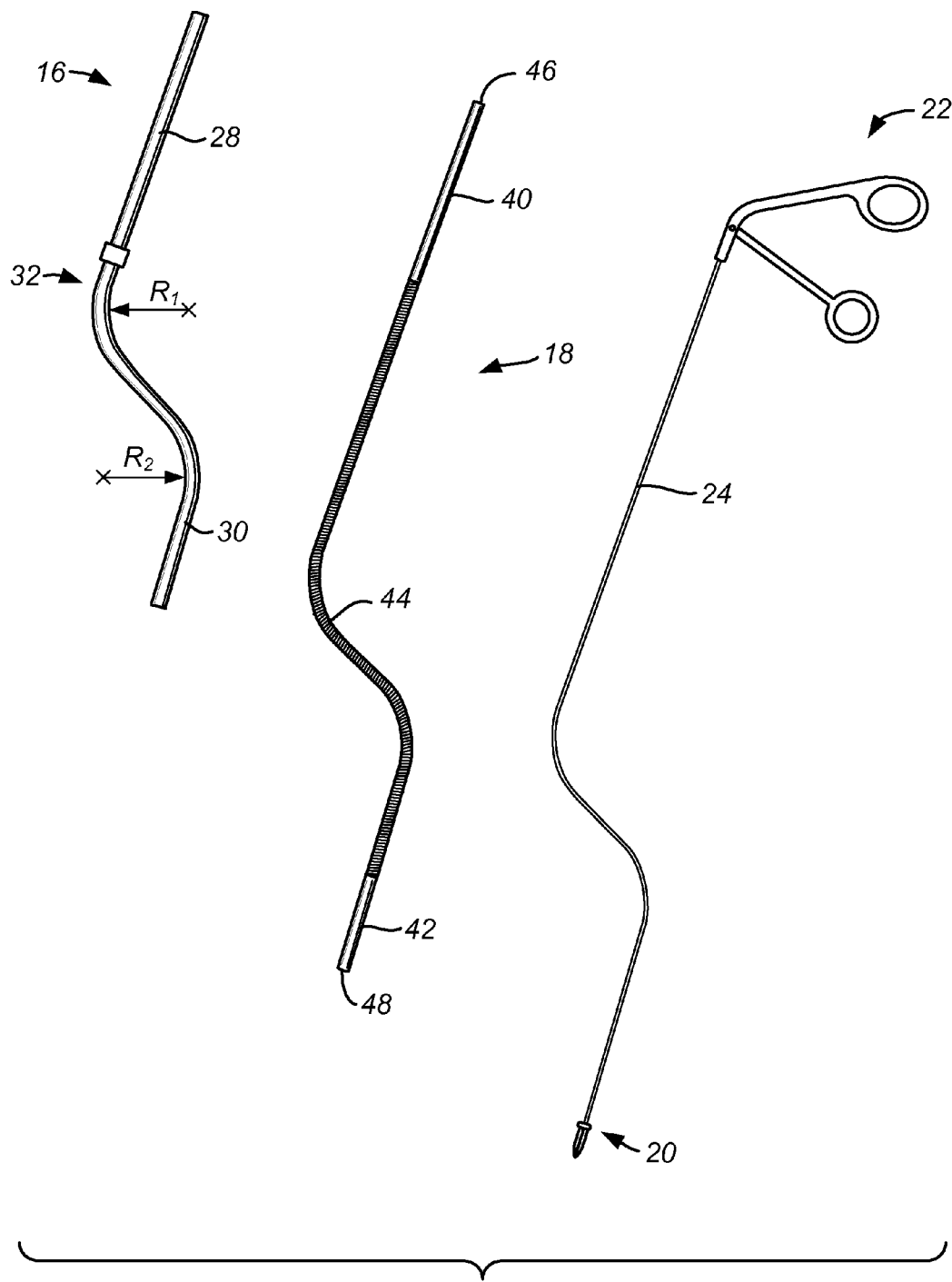
FIG. 4 is an exploded view of the tool of FIG. 3.
Figure 10A:
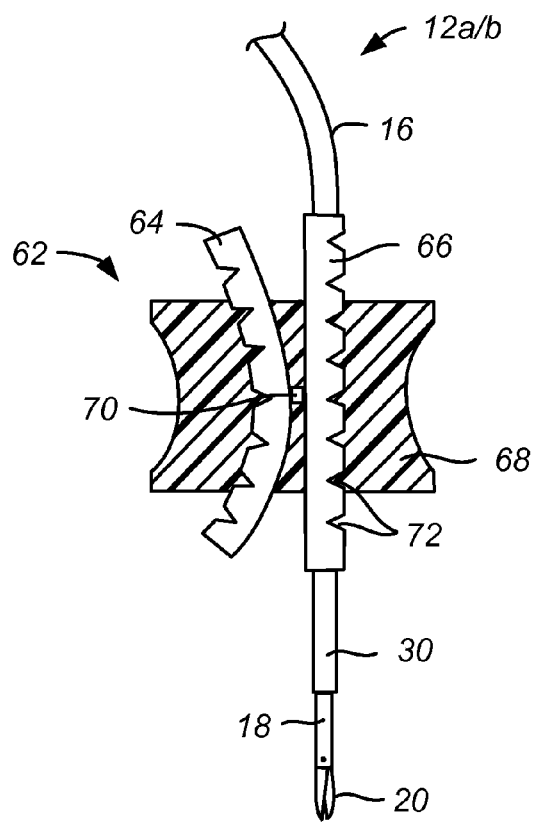
FIGS. 10A and 10B illustrate introduction of a laparoscopic tool in accordance with the principles of the present invention through the shapeable tube of the transcutaneous seal of FIG. 7.
Figure 10B:
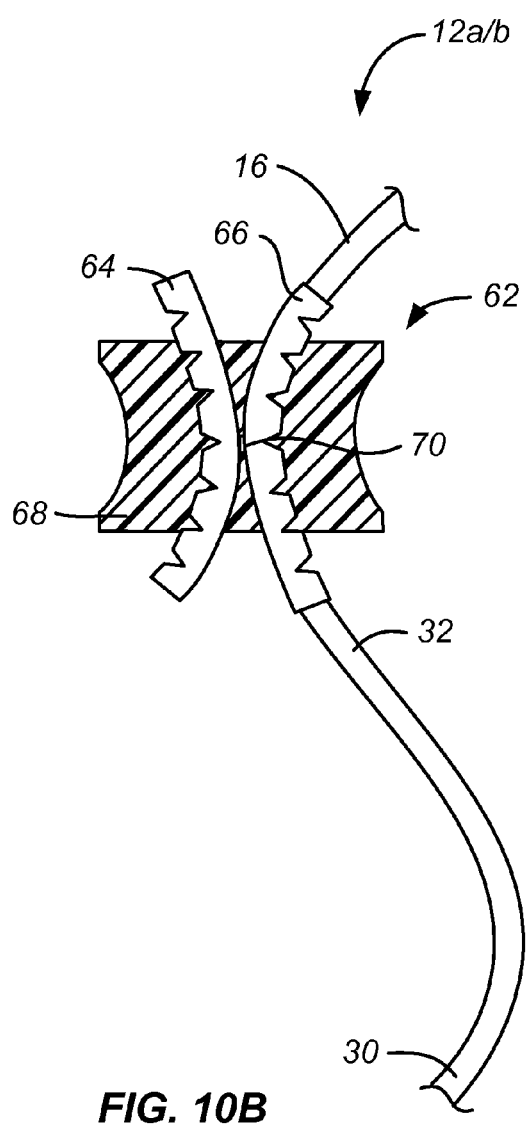

As illustrated in FIGS. 10A and 10B, a laparoscopic tool 12*a/b* as illustrated in FIG. 3, may be introduced through the shapeable tube 66. The straight distal region 30 of the tool 12*a/b* is introduced through the shapeable tube 66, causing the tube to straighten, as illustrated in FIG. 10A. The tube is sufficiently elastic to allow such opening, and the opening 72 further increases the bendability. As the tool 12*a/b* continues to be advanced through the transcutaneous seal 62, the curved middle region 32 enters the shapeable tube 66, causing the tube to bend back to its original conformation, as shown in FIG. 10B. At this point, the sleeve 16 may be locked to the shapeable tube 66 using any of the locking mechanisms described previously.

Figure 8:
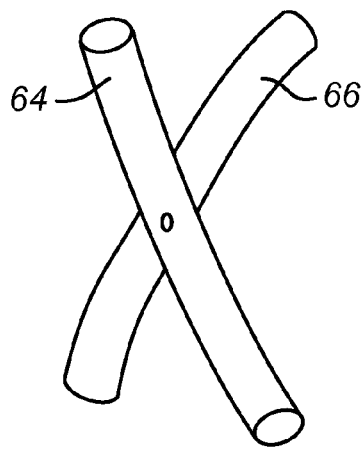
FIG. 8 and FIG. 9 illustrate the ability of the tubes of the transcutaneous seal of FIG. 7 to pivot relative to each other when the attachment is not fixed.
Figure 9:
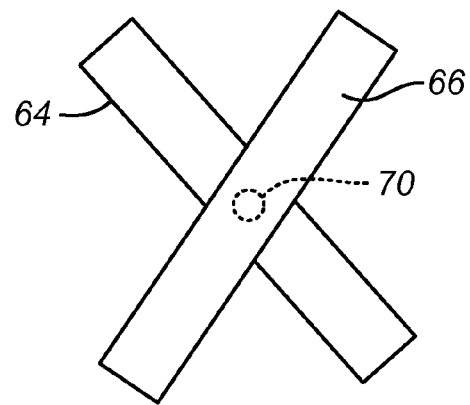

Referring now to FIGS. 11A-11C, a laparoscopic system 80 comprises a laparoscopic seal 82 having a first C-shaped tube 84 and a second C-shaped tube 86 extending in a generally vertical direction therethrough. The tubes will preferably but not necessarily have the shapeable configuration of the tubes illustrated in FIGS. 10A and 10B. The tubes 84 and 86 will also usually be pivotally attached, as illustrated in FIGS. 8 and 9, although they could also be fixedly attached as described with respect to other embodiments herein.

A first tool 88 comprises a rigid sleeve 90 having a straight proximal segment 92, a C-shaped middle segment 94, and a straight distal segment 96. A tool core 98, which may be constructed identically to the core 18 illustrated in FIG. 4, is slidably received in the sleeve 90 so that end effector 100 may be manipulated using handle 102, as generally described with respect to earlier embodiments of the invention. A second laparoscopic tool 104 may be identical to tool 88 (and for convenience has been given the same part reference numbers) but could also be any of the other tool constructions described previously in this application.

A particular advantage of the laparoscopic tool system 80 is that the individual tools 88 and 104 may be slidably moved within the C-shaped tubes 84 and 86, respectively. In particular, as shown in FIG. 11B, the second tool 104 has been rotated about a virtual insertion point 106 so that the effector 100 may be moved inwardly and outwardly relative to the effector 100 on the first tool 88. The first tool 88 may be similarly rotated about a second virtual insertion point 108, although the rotation is not illustrated. In this way, the tools may be manipulated by the two horizontally spaced-apart insertion points 106 and 108 in a manner which is very similar to manipulating tools which have been inserted through spaced-apart laparoscopic ports on the patient's abdomen or other body surface.

While it is desirable to rotate the tools about axes passing through the virtual insertion points 108, it is equally undesirable that the sleeves 90 of the tools be able to rotate within the C-shaped tubes of the laparoscopic seal 82. In order to further inhibit such alternative rotation, the C-shaped tube 86 may have a groove 109 formed in an inner surface of its central passage, as illustrated in FIG. 11C. The corresponding C-shaped middle region 96 of the tool sleeve 90 may then be provided with a ridge 110 which is received in the groove 108 to prevent any relative rotation of these two structures. The tools, however will usually be rotatable about a vertical axis through the seal 82 so that virtual insertion points 106 and 108 may be repositioned relative to the patient but remain fixed relative to each other.

Referring now to FIGS. 12A and 12B, it is also desirable that the C-shaped tubes 84 and 86 be able to pivot relative to each other. Thus, looking at a side view as shown in FIGS. 12A and 12B, the tools 88 and 90 may initially be disposed horizontally in the laparoscopic seal 82, as specifically shown in FIG. 12A. The user, however, may rotate the first tool 88 about a horizontal axis passing through the laparoscopic seal 82, as shown in FIG. 12B. The second tool 104 may be similarly rotated by pivoting the C-shaped tube 86 relative to the C-shaped tube 84, as shown in broken line in FIG. 12B. This further degree of freedom in the tool movement allows the treating physician still further ability to access different surgical targets while maintaining the spaced-apart virtual insertion points of the present invention.

Figure 13:
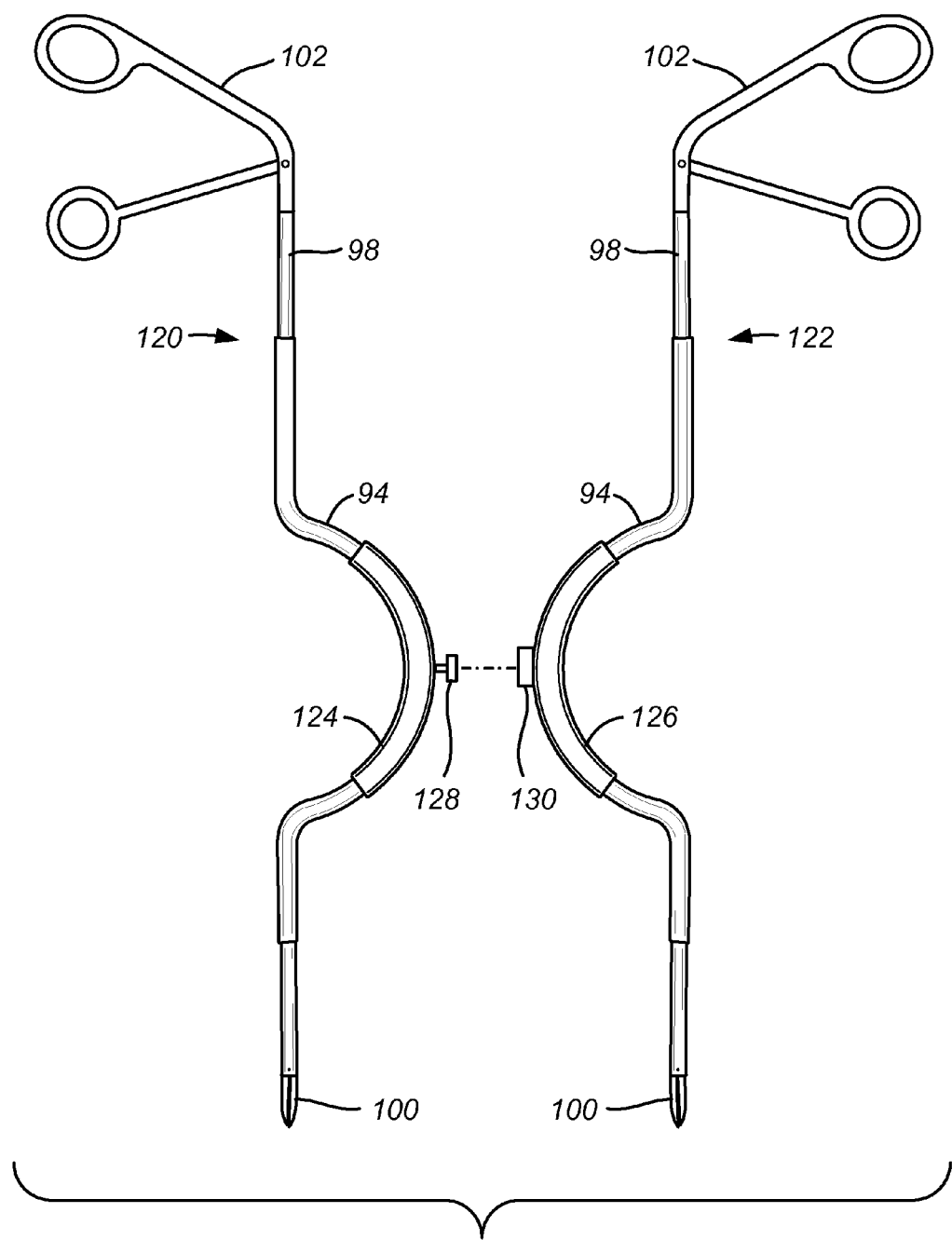
FIG. 13 illustrates a system including two tools with permanently mounted receiving tubes, where the tubes have coupling elements to permit their selective pivotal attachment.

As illustrated in FIG. 13, tools 120 and 122 are similar to the C-shaped tools 88 and 104 in FIGS. 11A and 11B except that C-shaped receiving tubes 124 and 126 are permanently (non-replaceably) placed over the C-shaped middle sections 94 of the sleeve 90. Thus, the receiving tubes 124 and 126 are in integral part of each tool in contrast to all earlier described embodiments where the tools are freely inserted into and removed from the receiving tubes, usually while the tubes are in place in a laparoscopic seal. Moreover, the tools will be able to slide freely within the receiving tubes 124 and 126 and the tubes will be pivotally attachable by male and female coupling elements 128 and 130, respectively. The receiving tubes are positioned and freely movable over the C-shaped mid-segment of each corresponding tool. The coupling elements 128 and 130 are located on the convex aspect of each tube 124 and 126, and the assembly of the pivot will occur at the time the tools are inserted through the seal. The integration of the C-shaped receiving tube of the seal with the C-shaped mid-segment 94 of the tool will further assure the match of the radius of these two components which will minimize friction and resistance during rotational movement of the tool. Note that, as described above, it will also be possible to provide universal coupling elements and/or hubs that allow all tubes to be connected to each other.

Figure 14A:
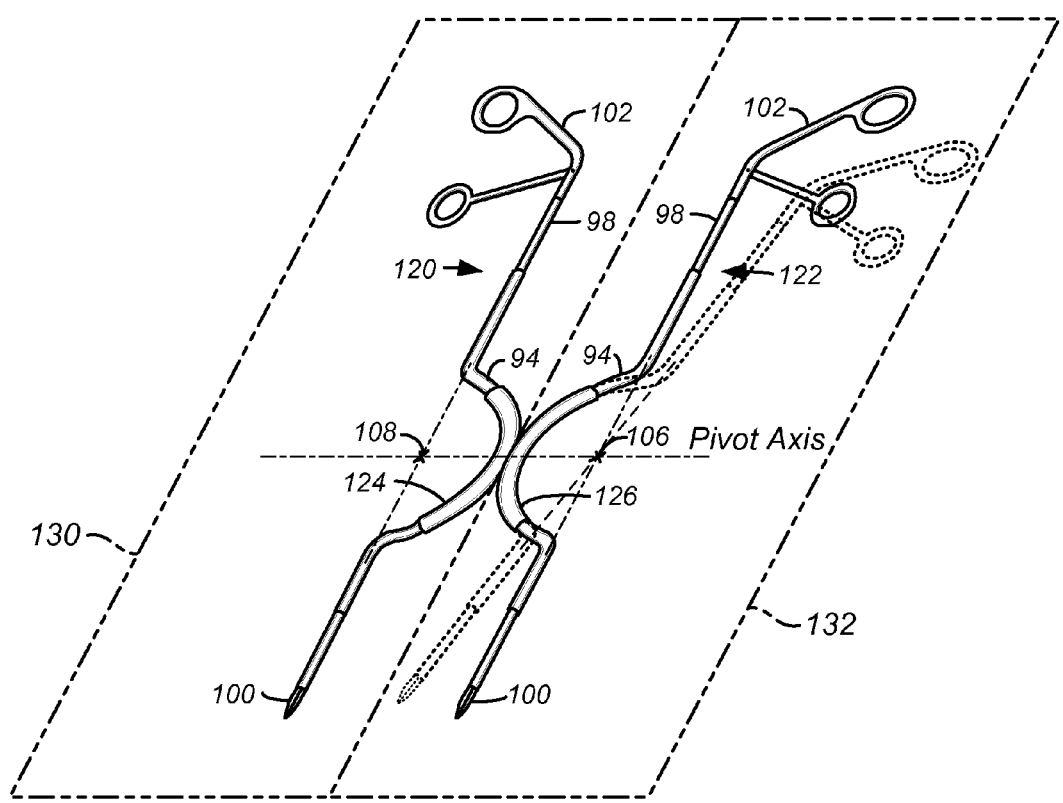
FIGS. 14A and 14B illustrate the tools of FIG. 13 being pivoted relative to each other in space.
Figure 14B:
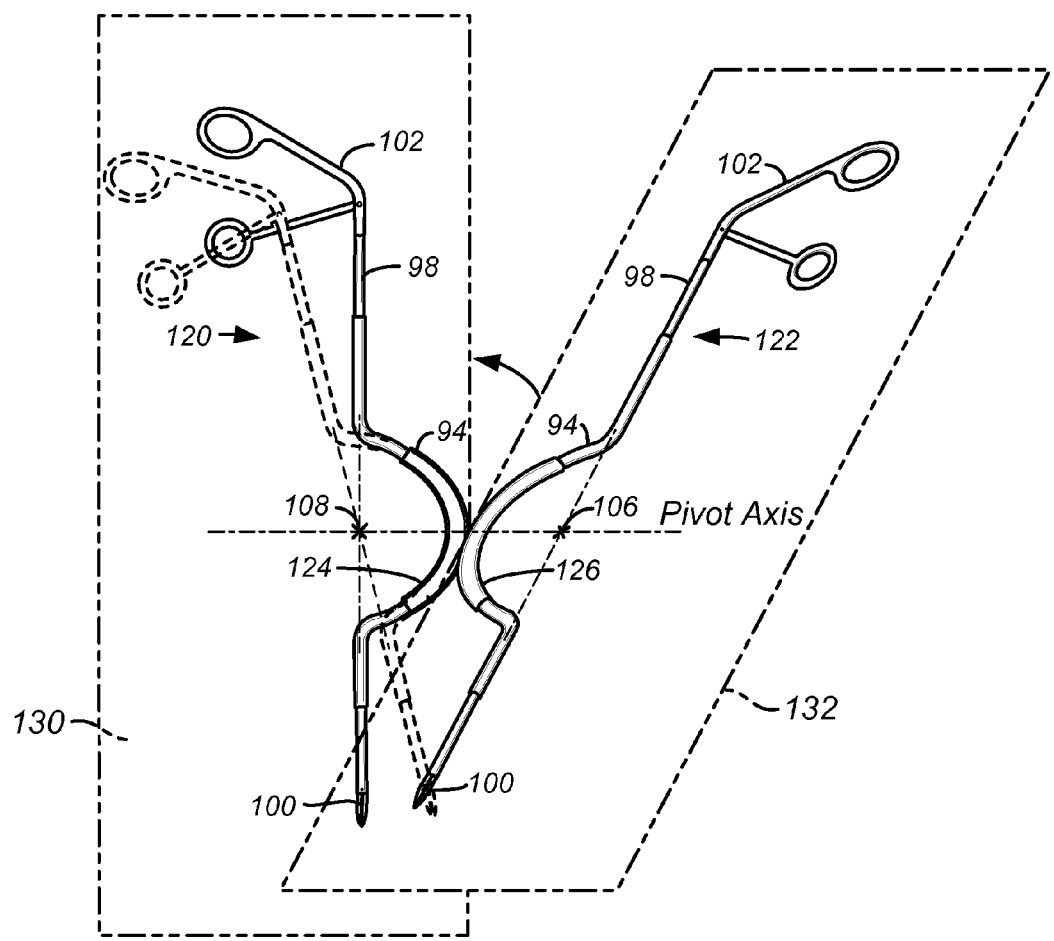

Referring now to FIGS. 14A and 14B, the ability of the tools 120 and 122 to be manipulated as though they were straight tools passing through the virtual insertion points 106 and 108 will be described. As seen in FIG. 14A, the receiving tubes 124 and 126 are pivotally attached so that the tools 120 and 122 always lie in planes 130 and 132 which are able to rotate relative to each other about a generally horizontal pivot axis. When the receiving tubes 124 and 126 are vertically aligned, the planes 130 and 132 of the tools will be co-planar, as illustrated in FIG. 14A. When the user moves the handles 102 of the tools 120 and 122 in opposite directions normal to the planes 130 and 132, the tools will move with the planes as shown in FIG. 14B. Such movement will be the same as if the tools were straight and passing through the virtual insertion points 106 and 108.

While both the receiving tubes 124 and 126 and the sleeves 94 of the tools will always remain within their respective planes 130 and 132, the core 98 and effector 100 of the tool may be moved laterally by manipulating the handle 102 to rotate the C-shaped middle segment 104 of the sleeve 94 within the respective receiving tube 106 or 108. Such movement is illustrated in FIG. 14A where the effector 100 can be moved laterally inwardly by moving the handle 102 laterally outward, as shown in broken line.

Thus, the user can place the effectors 100 at virtually any point within the operative field by manipulating the handles 102 just as they would if the tools were straight and passing through the virtual insertion points 106 and 108. Such an ability makes manipulating the tool much more intuitive and makes the experience of single port surgery much more like that of multiple port surgery.

Figure 15A:
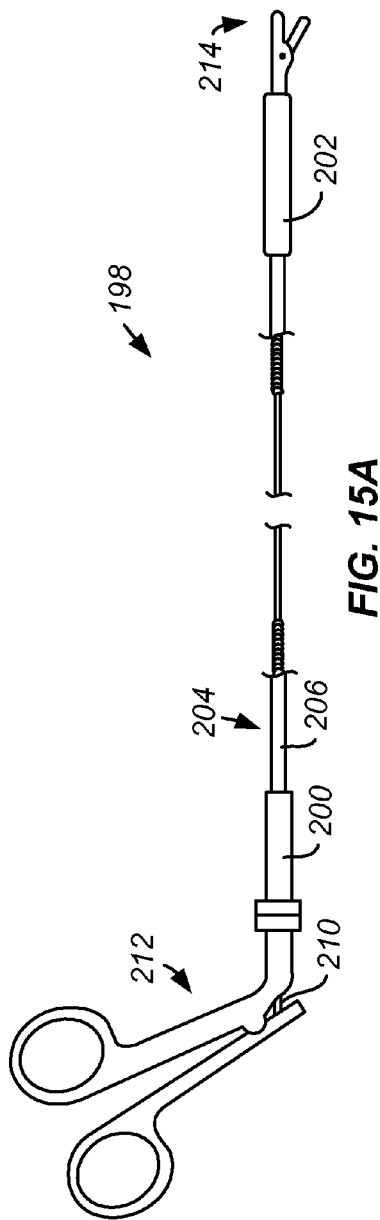
FIGS. 15A and 15B illustrate an exemplary tool core comprising nested beads encircling a pull cable.
Figure 15B:
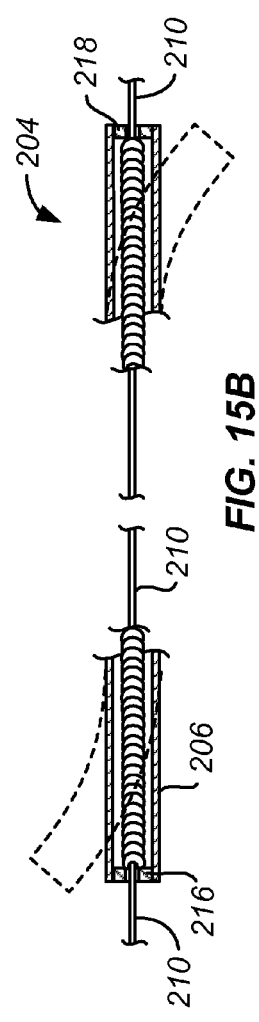

Referring now to FIGS. 15A and 15B, a tool core 198 which may be employed in any of the previously described S-shaped or C-shaped tools has an improved flexible central section which can be received in the non-linear sleeves of the previous embodiments. The tool core 198 includes a proximal, straight rigid section 200, a distal straight rigid section 202, and a substantially flexible central section 204 between said rigid sections. An exemplary construction of the flexible central section 204 is shown in FIG. 15B and includes a flexible outer tube 206, a plurality of nested beads 208, and a cable or pull wire 210 which extends through central passages in the beads allowing the handle 212 to proximally retract the cable 208 to actuate the tool 214, illustrated as a jaw-type tool.

The provision of two such independent "layers" surrounding the cable 210 has significant advantages. The nested beads 208 (where a spherical distal surface on the first bead nests in a concave receptacle in the distally adjacent bead) provides for flexible support of the cable to reduce the tendency of the cable to straighten while under tension when deploying the tool. The coaxially positioned outer tube 206 acts to both transmit torque and enhance pushability. Optionally, the flexible outer tube could be formed from a wire-reinforced plastic material to limit stretching of the flexible central section 204. The proximal-most and distal-most beads will be attached to proximal and distal end pieces 216 and 218, respectively, to hold the assembly together while the cable 210 is able to slide freely within the assembly.

Figure 16:
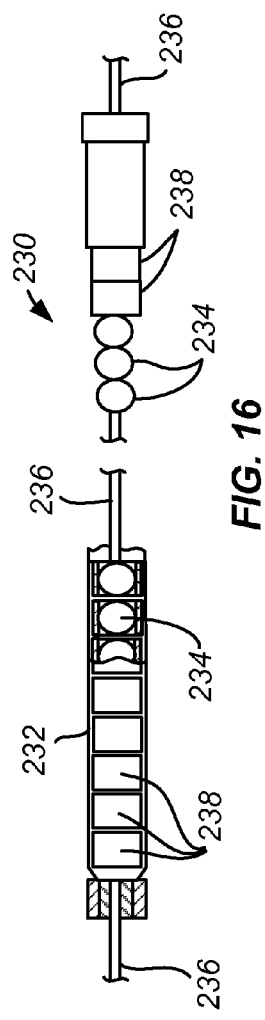
FIG. 16 illustrates an exemplary tool core comprising spherical beads positioned within cylindrical beads encircling a pull cable.

An alternative construction 230 of the flexible central section is illustrated in FIG. 16. The flexible central section 230 comprises an outer sheath 232, typically comprising a woven material with high tensile strength, and a plurality of inner spherical beads 234 each having a central passage for receiving a cable or pull wire 236. The spherical beads are each held within a cylindrical bead 238 to increase the pushability of the flexible central section without compromising flexibility. As with the previous embodiments, the cable or pull wire 236 is able to freely translate within the flexible central section even when the section is bent by any of the deployment assemblies described hereinbefore.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for performing a laparoscopic procedure on a patient, said method comprising:
   (a) providing a tool system which includes:
   a pair of laparoscopic tool assemblies, each tool assembly having:
      (i) a tubular sleeve with (i) a substantially straight proximal region defining an axis, (ii) a middle semi-circular C-shaped region having a proximal end attached to and extending from the proximal region, a distal end, and a C-shaped curve between the proximal and distal ends, and (iii) a substantially straight distal region extending from the middle region and a central passage therethrough, wherein the proximal region and the distal region are aligned along said axis, wherein the proximal and distal regions can telescope to vary an extension length of the tool;
      (ii) a core disposed in the sleeve and having a proximal section extending from the proximal region of the sleeve and a distal section extending from the distal region of the sleeve, wherein the core can be rotated and axially extended and retracted relative to the sleeve;
      (iii) a C-shaped coupling tube, wherein the C-shaped curve of the tubular sleeve is slidably received in the C-shaped coupling tube; and
      (iv) an effector at the distal end of the core on each laparoscopic tool;
   (b) placing a single port through the patient's abdominal wall,
   (c) pivotally coupling the C-shaped coupling sleeves of the assemblies to each other at a pivot location on the C-shaped coupling sleeves within the single access port so that the axis of each tool passes through a virtual insertion point at a center of the semi-circular C-shaped middle region and the tools, wherein such pivotal coupling of the laparoscopic tool assemblies constrains the tool assemblies to pivot in planes relative to each other about a horizontal pivot axis, wherein the virtual insertion points are spaced apart along the horizontal pivot axis; and
   (d) manipulating a handle on each tool to (i) advance the core in and out of the sleeve, (ii) slide the C-shaped curve of the sleeve within the C-shaped coupling tube, (iii) pivot the tools relative to each other about the horizontal pivot axis while each tool remains within its respective plane, (iv) telescope the proximal and distal regions to vary an extension length of the tool while the center point of the C-shaped middle region of the tubular sleeve remains at the virtual insertion point, and (v) manipulate the end effector, wherein the pivot location between the C-shaped coupling sleeves remains within the single port with the distal end of each tool within the patient's abdominal cavity as the handles are manipulated.

2. A method as in claim 1, wherein pivotally coupling comprises engaging a pivotal attachment element on a center region of the C-shaped coupling sleeve of a first tool of the pair of tools to a pivotal attachment element on a center region of the C-shaped coupling sleeve of a second tool of the pair of tools.

3. A method as in claim 2, wherein the pivotal attachment elements are detachably coupled to each other.

4. A method as in claim 1, wherein the core comprises a drive cable coupled at a proximal end to the handle which passes through a central passage of the core and is coupled at a distal end to the effector, further comprising pulling and/or rotating the drive cable to actuate the effector.

5. A method as in claim 4, wherein the core comprises a tubular body which is received in the central passage of the tubular sleeve, wherein at least a central section of the body which is disposed within the sleeve is flexible to allow the body to be advanced and retracted within the curves of the middle region of the sleeve.

6. A method as in claim 5, wherein the proximal and distal sections of the core are substantially rigid.

7. A method as in claim 6, wherein the central section comprises nested elements which are coupled to transmit torque but permit bending.

8. A method as in claim 7, wherein the cable passes through aligned openings in the nested elements.

9. A method as in claim 1, wherein the effector comprises an electrode which is connected to an electrical conductor which passes through a central passage of the core.

* * * * *